(12) United States Patent
Chao et al.

(10) Patent No.: US 7,418,978 B2
(45) Date of Patent: Sep. 2, 2008

(54) METHODS AND APPARATUS FOR PROVIDING FLUID TO A SEMICONDUCTOR DEVICE PROCESSING APPARATUS

(75) Inventors: Sandy Shih-Hsun Chao, Campbell, CA (US); Songjae Lee, San Jose, CA (US); Ho Seon Shin, Cupertino, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 11/048,106

(22) Filed: Jan. 28, 2005

(65) Prior Publication Data

US 2005/0284528 A1    Dec. 29, 2005

Related U.S. Application Data

(60) Provisional application No. 60/540,540, filed on Jan. 30, 2004.

(51) Int. Cl.
*F16K 11/20* (2006.01)

(52) U.S. Cl. .................... 137/884; 137/597; 451/101

(58) Field of Classification Search ............. 137/606, 137/597, 563, 884; 451/101
See application file for complete search history.

(56) References Cited

U.S. PATENT DOCUMENTS

| | | | | |
|---|---|---|---|---|
| 3,572,366 | A | * | 3/1971 | Wiggins ............... 137/240 |
| 4,000,684 | A | | 1/1977 | Ruffley |
| 4,505,294 | A | | 3/1985 | Walter |
| 4,627,465 | A | * | 12/1986 | Kolibas et al. ........... 137/563 |
| 5,558,249 | A | | 9/1996 | Falcoff |
| 5,605,179 | A | * | 2/1997 | Strong et al. ............ 137/884 |
| 5,709,593 | A | | 1/1998 | Guthrie et al. |
| 5,819,783 | A | | 10/1998 | Blatt et al. |
| 5,993,647 | A | | 11/1999 | Huang et al. |
| 6,102,782 | A | | 8/2000 | Custer et al. |
| 6,148,851 | A | | 11/2000 | Friedline et al. |
| 6,149,508 | A | | 11/2000 | Vanell et al. |
| 6,336,845 | B1 | | 1/2002 | Engdahl et al. |
| 6,416,385 | B2 | | 7/2002 | Ferri et al. |
| 6,425,802 | B1 | | 7/2002 | Custer et al. |
| 6,431,957 | B1 | | 8/2002 | Lefky |
| 6,440,379 | B1 | | 8/2002 | Verrill et al. |

(Continued)

FOREIGN PATENT DOCUMENTS

JP        60139962        1/1987

(Continued)

Primary Examiner—John Fox
(74) Attorney, Agent, or Firm—Dugan & Dugan

(57) ABSTRACT

In a first aspect, a valve assembly is provided that includes a valve assembly output adapted to output at least one of DI water and a chemical. A first valve of the valve assembly includes (1) a first input adapted to receive the chemical; (2) a first output adapted to circulate the chemical to a chemical return; and (3) a second output adapted to output the chemical to the valve assembly output. The valve assembly also includes a second valve positioned downstream from the first valve. The second valve includes (1) an input adapted to receive deionized (DI) water; and (2) an output adapted to output DI water to the valve assembly output. A check valve is coupled between the second output of the first valve and the output of the second valve, and the first valve, second valve and check valve are included in a single manifold.

8 Claims, 4 Drawing Sheets

U.S. PATENT DOCUMENTS

| | | |
|---|---|---|
| 6,517,418 B2 | 2/2003 | Engdahl et al. |
| 6,889,709 B2 * | 5/2005 | Hanada et al. .............. 137/606 |
| 2001/0009652 A1 | 7/2001 | Arno |
| 2004/0213721 A1 | 10/2004 | Arno et al. |

FOREIGN PATENT DOCUMENTS

| | | |
|---|---|---|
| JP | 10015117 | 7/1999 |
| JP | 11130150 | 11/2000 |
| JP | 2000304485 | 4/2002 |

* cited by examiner

METHODS AND APPARATUS FOR PROVIDING FLUID TO A SEMICONDUCTOR DEVICE PROCESSING APPARATUS

The present application claims priority from U.S. Provisional Patent Application Ser. No. 60/540,540, filed Jan. 30, 2004, which is hereby incorporated by reference herein in its entirety.

FIELD OF THE INVENTION

The present invention relates generally to semiconductor device manufacturing, and more particularly to methods and apparatus for providing fluid to a semiconductor device processing apparatus.

BACKGROUND OF THE INVENTION

While manufacturing a semiconductor device, a substrate may be processed by a semiconductor device processing apparatus, such as a polishing device. A polishing device may dispense a fluid, such as a chemical (e.g., a slurry) or water (e.g., deionized (DI) water), to the substrate being processed. To supply chemicals and/or DI water to a polishing device, a plurality of valves that form a valve system may be employed. Generally, a plurality of separate valves are coupled together to form the valve system. The use of separate valves, however, is costly and non-compact. Such a valve system typically cannot be included in a polishing device. Accordingly, improved methods and apparatus are desired for providing fluid to a semiconductor device processing apparatus.

SUMMARY OF THE INVENTION

In a first aspect of the invention, a valve assembly is provided. The valve assembly is adapted to provide fluid to a semiconductor device processing apparatus and includes a valve assembly output adapted to output at least one of DI water and a chemical. A first valve of the valve assembly includes (1) a first input adapted to receive the chemical; (2) a first output adapted to circulate the chemical to a chemical return; and (3) a second output adapted to output the chemical to the valve assembly output. The valve assembly also includes a second valve positioned downstream from the first valve. The second valve includes (1) an input adapted to receive deionized (DI) water; and (2) an output adapted to output DI water to the valve assembly output. A check valve is coupled between the second output of the first valve and the output of the second valve. The first valve, second valve and check valve are included in a single manifold.

In a second aspect of the invention, a fluid dispensing system is provided. The fluid dispensing system is adapted to provide fluid to a semiconductor device processing apparatus and includes a plurality of the above described valve assemblies within a single manifold.

In a third aspect of the invention, a semiconductor device processing apparatus is provided that includes a polishing device and a valve assembly coupled to the polishing device. The valve assembly is adapted to provide fluid to the polishing device and includes a valve assembly output adapted to output at least one of DI water and a chemical to the polishing device. A first valve of the valve assembly includes (1) a first input adapted to receive the chemical; (2) a first output adapted to circulate the chemical to a chemical return; and (3) a second output adapted to output the chemical to the valve assembly output. The valve assembly also includes a second valve positioned downstream from the first valve. The second valve includes (1) an input adapted to receive deionized (DI) water; and (2) an output adapted to output DI water to the valve assembly output. A check valve is coupled between the second output of the first valve and the output of the second valve. The first valve, second valve and check valve are included in a single manifold. Numerous other aspects are provided, as are methods in accordance with these other aspects of the invention.

Other features and aspects of the present invention will become more fully apparent from the following detailed description, the appended claims and the accompanying drawings.

DETAILED DESCRIPTION

The present invention relates to reducing the space occupied by (e.g., footprint) and cost of a fluid dispensing system for providing or dispensing fluid to a semiconductor device processing apparatus. Further, the volume of dead legs included in the fluid dispensing system is greatly reduced when compared to conventional fluid dispensing systems.

Figure 1:
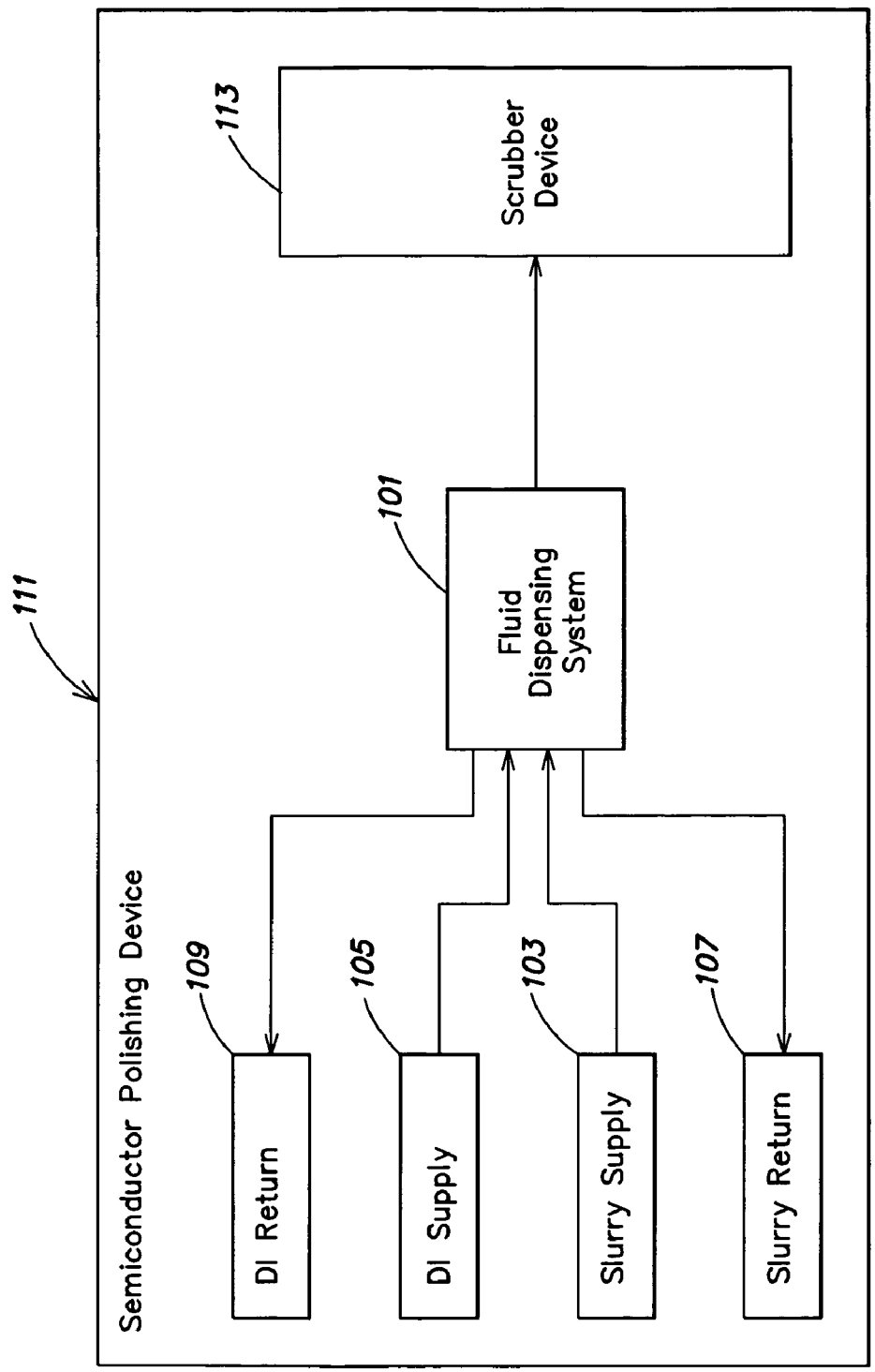
FIG. 1 illustrates an exemplary fluid dispensing system in accordance with an embodiment of the present invention.

FIG. 1 illustrates an exemplary fluid dispensing system in accordance with an embodiment of the present invention. With reference to FIG. 1, the fluid dispensing system 101 is coupled to a chemical source 103, such as a slurry supply. The fluid dispensing system 101 receives a chemical (e.g., slurry) output from the chemical source 103. Similarly, the fluid dispensing system 101 is coupled to a supply of water (e.g., deionized (DI) water) 105 and receives DI water output from the supply of water 105. The fluid dispensing system 101 also is coupled to a chemical return 107 and a DI water return 109. When the fluid dispensing system 101 is not using the chemical received from the chemical source 103 and/or the DI water received from the supply of DI water 105, the fluid dispensing system 101 may circulate the chemical and/or the DI water by outputting the chemical and/or DI water to the chemical return 107 and/or the DI water return 109, respectively.

In one embodiment, the fluid dispensing system 101 is coupled to and included in a semiconductor device processing apparatus 111, such as a polishing device for performing chemical mechanical polishing. In other embodiments, the fluid dispensing system 101 may be external to the semiconductor device processing apparatus 111. Assuming that the semiconductor device processing apparatus 111 is a polishing device, the semiconductor polishing device 111 may include and/or be coupled to a scrubbing device 113 for removing polishing chemicals and particulates from the surface of a substrate being processed by the polishing device 111. An output of the fluid dispensing system 101 is coupled to the scrubber device 113 and provides the chemical and/or DI water to the scrubber device 113 during substrate processing.

Figure 2:
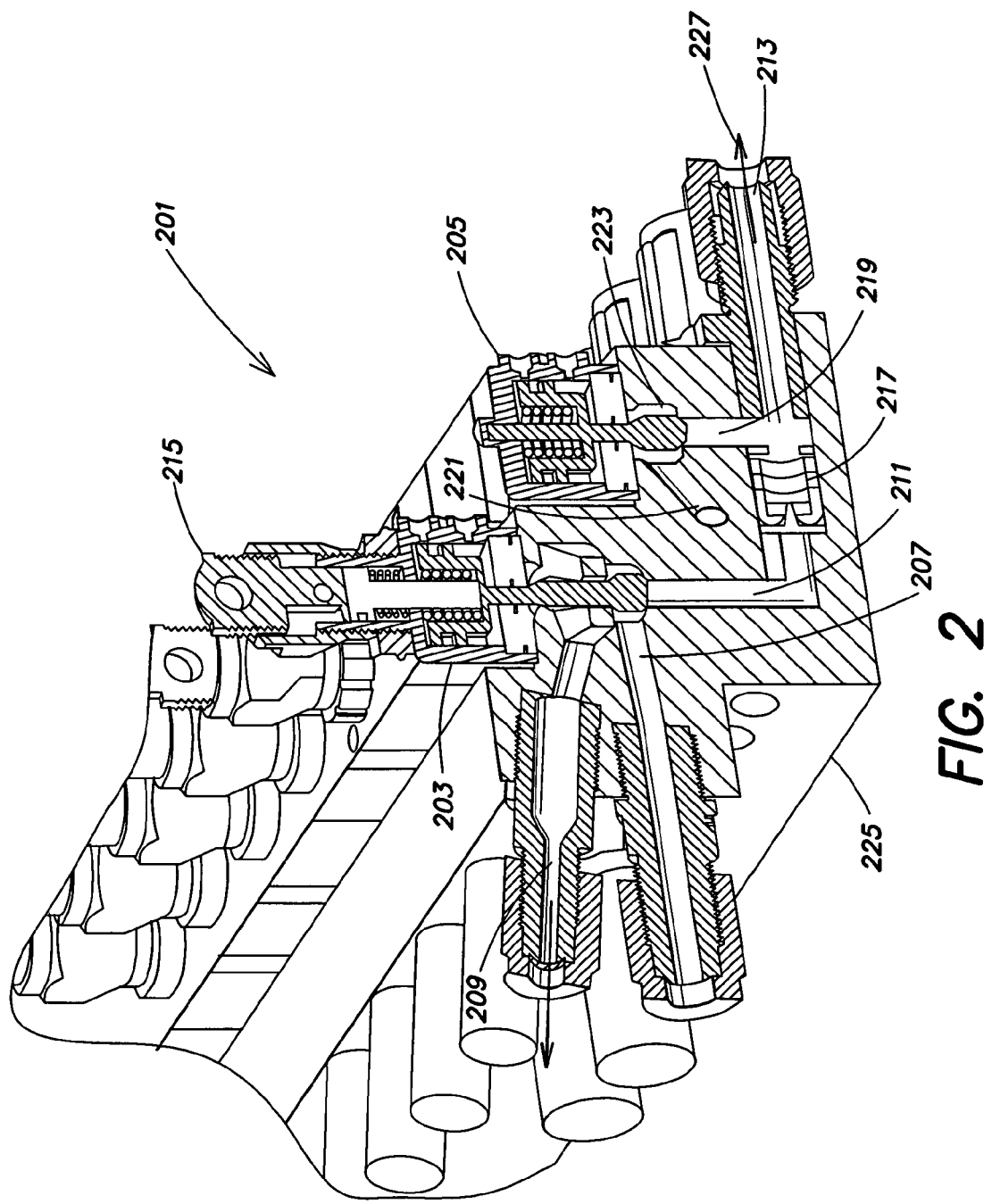
FIG. 2 is a cross-sectional schematic representation of a valve assembly included in the fluid dispensing system in accordance with an embodiment of the present invention.

FIG. 2 is a cross-sectional schematic representation of a valve assembly 201 included in the fluid dispensing system 101 in accordance with an embodiment of the present invention. The valve assembly 201 is adapted to receive fluid and output (e.g., provide) fluid to the semiconductor device processing apparatus 111. With reference to FIG. 2, the valve assembly 201 includes a first valve 203 coupled to a second valve 205. The first valve 203 is adapted to (1) receive a chemical from the chemical source or supply 103 and circulate the chemical to the chemical return 107; or (2) output the chemical to the semiconductor device processing apparatus 111. More specifically, the first valve 203 includes a first input 207 adapted to couple to the chemical source 103 and receive the chemical from the chemical source 103. The first valve 203 includes a first output 209 (e.g., a chemical-return output) adapted to couple to the chemical return 107 and circulate the chemical by outputting the chemical to the chemical return 107. The size (e.g., diameter) of the first output 209 may be smaller than the size of the first input 207 to provide increased back pressure. Further, the first valve 203 includes a second output 211 adapted to output the chemical toward an output 213 of the valve assembly 201. Therefore, in the embodiment shown, the first valve 203 is a three-way valve with one input and two outputs. Valves of different configurations and/or types may be employed as the first valve 203.

The first valve 203 includes a manual override switch 215 (e.g., a tap) adapted to prevent the first valve 203 from outputting the chemical from the second output 211. Therefore, actuating (e.g., turning on) the manual override switch 215 may prevent (e.g., lock out) one or more components of the semiconductor device processing apparatus 111 to which the valve assembly 201 is coupled from receiving the chemical until the manual override switch 215 is turned off. In one embodiment, the default setting of the manual override switch 215 is on, which prevents one or more components of the semiconductor device processing apparatus 111 from receiving the chemical. In other embodiments, the default setting of the manual override switch 215 may be off. It should be noted that the first valve 203 of the valve assembly 201 incorporates the functionality of two valves (e.g., a manual valve and three-way valve) into a single valve, thereby minimizing the space required by the valve assembly 201.

The valve assembly 201 includes a second valve 205 coupled to the first valve 203 via a check valve 217. The check valve 217 is adapted to permit a one-way flow of fluid in the valve assembly 201 (as described below). The second valve 205 is positioned downstream from the first valve 203. More specifically, the second output 211 of the first valve 203 is coupled to an output 219 of the second valve 205 via the check valve 217.

The second valve 205 is adapted to receive and output DI water. More specifically, the second valve 205 includes an input 221 adapted to couple to the DI water supply 105 and receive DI water from the DI water supply 105 of the fluid dispensing system 101. The output 219 of the second valve 205 is coupled to the output 213 of the valve assembly 201 and adapted to output DI water thereto. In one embodiment, the second valve 205 is a two-way valve. However, different configurations and/or types of valves may be employed as the second valve 205.

As shown in FIG. 2, the output 213 of the valve assembly 201 is coupled to the first valve 203 (e.g., via the second output 211 of the first valve 203) and to the second valve 205 (e.g., via the output 219 of the second valve 205). The output 213 of the valve assembly 201 is adapted to output (e.g., dispense) the chemical, which is received from the first valve 203, and/or DI water, which is received from the second valve 205, from the valve assembly 201 to the semiconductor device processing apparatus 111.

The valve assembly 201 may include a DI water return output (not shown in FIG. 2, but see reference numeral 301 in FIG. 3) coupled to the second valve 205 and adapted to couple to the DI return 109 and circulate DI water by outputting the DI water to the DI return 109. Before being output from the DI-water-return output, the DI water received in the valve assembly 201 travels along a DI water circulation path 223.

In one embodiment, one or more of the first and second valves 203, 205 are pneumatically-actuated valves. However, other types of valves may be employed.

As shown in FIG. 2, the first valve 203, second valve 205 and check valve 217 are included in or formed as a single manifold (e.g., valve manifold 225). In this manner, the space occupied by the valve assembly 201, and therefore, the fluid dispensing system 101, is reduced compared to conventional fluid dispensing systems. Further, including the first valve 203, second valve 205 and check valve 217 in the valve manifold 225 reduces the number of fittings (e.g., flare or other suitable fittings) required to receive the chemical in and/or dispense the chemical from the fluid dispensing system 101. The number of potential leakage points thereby is reduced.

The operation of the valve assembly 201 (and the fluid dispensing system 101) is now described with reference to FIG. 2. During operation, the valve assembly 201 receives a chemical. More specifically, the first input 207 of the first valve 203 receives the chemical from the chemical supply 103. When the first valve 203 is closed (e.g., via the manual override switch 215 or pneumatically), the first valve 203 outputs the chemical from the first output 209 (e.g., a chemical return output) of the first valve 203. In this manner, the chemical is circulated from the chemical supply 103 to the chemical return 107. The circulation of the chemical prevents conglomeration and/or settling of the chemical within the first valve 103 (so as to reduce wafer defects which may be caused by such conglomeration/settling).

While the first valve 203 is closed, the second output 211 of the first valve 203 does not output the chemical. Note that the volume between the second output 211 of the first valve 203 and the check valve 217 may include stagnant chemicals output by the first valve 203 before the first valve 203 was closed. That is, the volume between the second output 211 of the first valve 203 and the check valve 217 may be a dead leg. However, because the dead leg is located within the manifold 225, its volume is relatively small.

Alternatively, when the first valve 203 is open, the first valve 203 may output the chemical from the second output 211 of the first valve 203 toward the check valve 217. The check valve 217 permits a one-way flow of fluid from the first valve 203 through the check valve 217 and toward the output 213 of the valve assembly 201. (It is assumed the second valve 205 is closed. As described below, the second valve 205 may be closed while the first valve 203 is open to avoid contaminating the DI water supply with the chemical.) Thereafter, the valve assembly 201 dispenses the chemical from the output 213 (e.g., valve manifold output) of the valve assembly 201. For example, the valve assembly 201 and, therefore, the fluid dispensing system 101 may dispense the chemical to a polishing device component, such as the scrubber device 113.

Further, during operation, the valve assembly 201 receives DI water. More specifically, the input 221 of the second valve 205 receives DI water from the DI water supply 105, for example, via a DI water input 220 (FIG. 3) of the fluid dispensing system 101. When the second valve 205 is closed (e.g., pneumatically), the DI water received by the valve assembly 201 circulates along the DI-water circulation path 223 toward the DI-water-return output (not shown in FIG. 2; 301 in FIG. 3). Alternatively, when the second valve 205 is open, the second valve 205 outputs the DI water from the output 219 of the second valve 205 toward the check valve 217 and/or the output 213 of the valve assembly 201. Because the check valve 217 permits only a one-way flow of fluid, and the second valve 205 is positioned downstream from the check valve 217, the check valve 217 prevents the DI water from the output 219 of the second valve 205 from reaching the first valve 203. DI water thereby is prevented from contaminating the chemical supply 103 or the chemical return 107.

The DI water output from the output 219 of the second valve 205 travels toward the output 213 of the valve assembly 201 along an output path 227 of the valve assembly 201. The DI water may serve to purge portions of the valve assembly 201 (e.g., the path 227). Thereafter, the valve assembly 201 dispenses the DI water from the output 213 (e.g., valve manifold output) of the valve assembly 201. For example, the valve assembly 201 and, therefore, the fluid dispensing system 101 may dispense the DI water to a scrubber device 113 of a polishing device. Because DI water may flow along the DI water circulation path 223 and through the DI water return output (not shown in FIG. 2; 301 in FIG. 3) while the second valve 205 is closed, and along output path 227 and through the output 213 of the valve assembly 201 when the second valve 205 is open, no DI water dead legs exist.

In one embodiment, the second valve 205 is closed while the first valve 203 is open. In this manner, the chemical output by the second output 211 of the first valve 203 toward the output 213 of the valve assembly 201 may be prevented from contaminating the DI water supply 105 and/or the DI water return 109. Further, the DI water may be prevented from diluting the chemical. The valve assembly 201 dispenses the chemical from the output 213 of the valve assembly 201 to a component of the semiconductor device processing apparatus 111.

The second valve 205 may be open while the first valve 203 is closed. In this manner, the valve assembly 201 dispenses DI water from the output 213 of the valve assembly 201 to a component of the semiconductor device processing apparatus 111, and circulates the chemical from the first output 209 of the first valve 203 to the chemical return 107.

Alternatively, the first 203 and second valves 205 both may be closed. In this manner, the valve assembly 201 circulates the chemical and DI water to the chemical return 107 and the DI water return 109, respectively. Other combinations of states (e.g., on or off) may be employed for the first valve 203 and second valve 205. Altering the states of the first valve 203 and/or second valve 205 enables a user to employ the valve assembly 201 to selectively supply the chemical to one or more components of a semiconductor device processing apparatus 111. The states of the first valve 203 and/or second valve 205 may be altered using two actuators (e.g., an actuator corresponding to each of the first valve 203 and second valve 205). Other numbers of actuators may be used.

Figure 3:
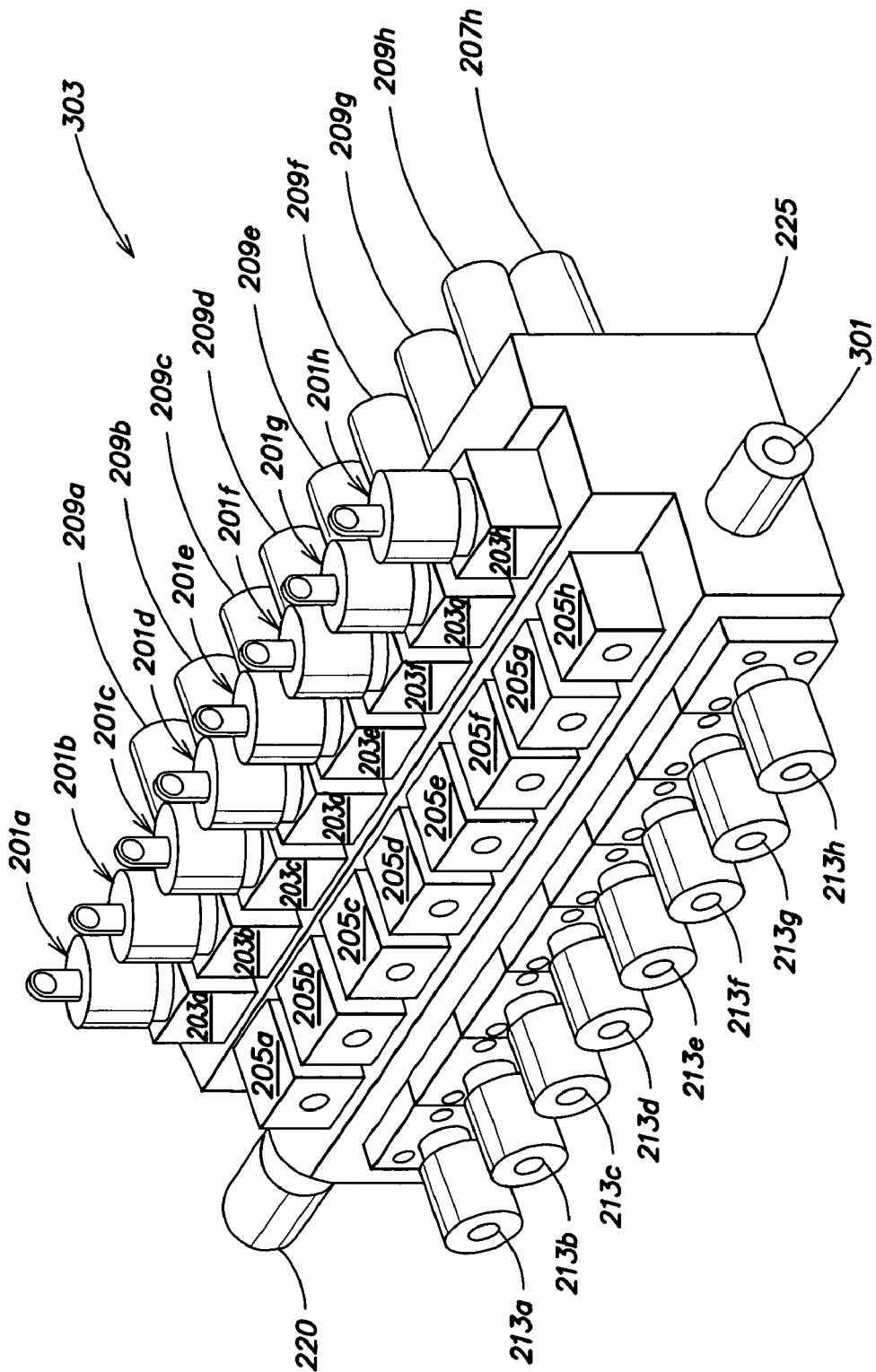
FIG. 3 is a schematic representation of a second exemplary fluid dispensing system in accordance with an embodiment of the present invention.

FIG. 3 is a schematic representation of a second exemplary fluid dispensing system 303 in accordance with an embodiment of the present invention. The second exemplary fluid dispensing system 303 includes a plurality of the valve assemblies 201a-h of FIG. 2 coupled together. Each of the plurality of valve assemblies 201a-h are included or formed in the same manifold 225. Therefore, the space occupied by the second exemplary fluid dispensing system 303 is smaller than that occupied by conventional fluid dispensing systems. Each of the plurality of valve assemblies 201a-h may be (1) coupled to a chemical supply 103 via a respective first input 207a-h (only 207h is shown in FIG. 3); (2) coupled to a chemical return 107 via a respective first output 209a-h; and (3) coupled to a respective component of a semiconductor device processing apparatus 111 via a respective output 213a-h of the valve assembly 201a-h. Two or more of the plurality of valve assemblies 201a-h may be coupled to the same or different chemical supplies, chemical returns and/or semiconductor device processing apparatus components. Although in one embodiment, the second exemplary fluid dispensing system 303 includes eight valve assemblies 201a-h, the second exemplary fluid dispensing system 303 may include a larger or smaller number of valve assemblies 201.

The second exemplary fluid dispensing system 303 includes a DI water input 220 adapted to couple to and receive DI water from the DI supply 105 and a DI-water-return output 301 adapted to couple to and circulate DI water to the DI water return 109. For example, the input of the second valve 205a of the valve assembly 201a adjacent a first end of the manifold 225 may serve as or be coupled to the DI water input 220 of the second exemplary fluid dispensing system 303. The inputs of the second valves of the remaining valve assemblies 201b-h may be similarly coupled to the DI-water input 220. Similar to the DI water circulation path 223 of the valve assembly 201 of FIG. 2, the second exemplary fluid dispensing system 303 may include a DI water circulation path, for example, through one or more (e.g., each of) the second valves 205a-h of the plurality of valve assemblies 201a-h. The operation of the second exemplary fluid dispensing system 303 is similar to that of the first exemplary fluid dispensing system 101 of FIG. 2 and is not described herein.

By providing and employing the second exemplary fluid dispensing system 303, one or more chemicals and/or DI water may be selectively dispensed (e.g., supplied) to one or more components of the semiconductor device processing apparatus 111. The one or more chemicals and/or DI water also may be circulated to respective chemical returns and/or a DI water return. The footprint, cost, and size and number of dead legs in fluid circulation paths of the second exemplary fluid dispensing system 303 thereby are reduced.

Figure 4:
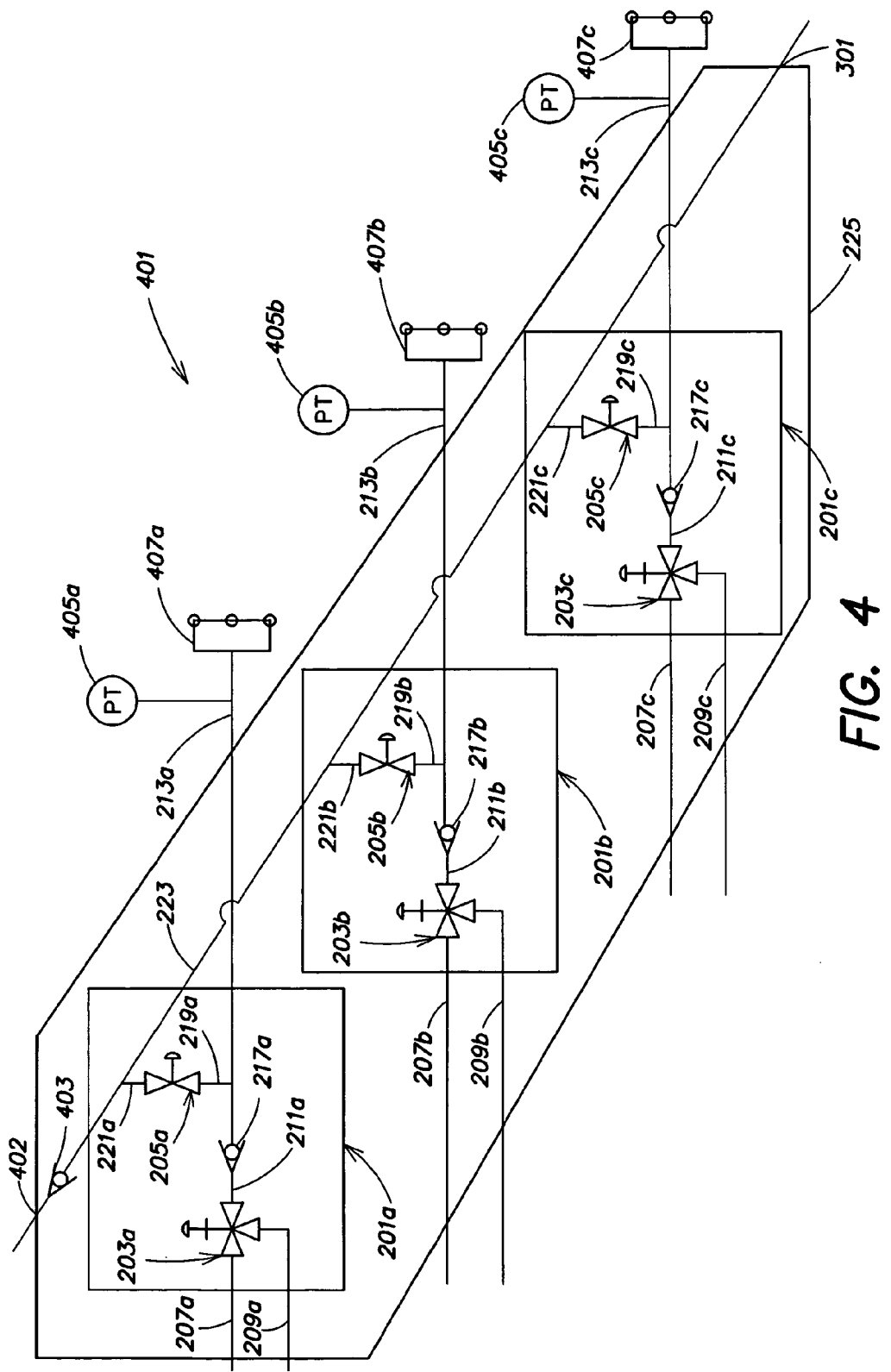
FIG. 4 is a block diagram of a third exemplary fluid dispensing system, which is an alternative embodiment of the second exemplary fluid dispensing system.

FIG. 4 is a block diagram of a third exemplary fluid dispensing system 401, which is an alternative embodiment of the second exemplary fluid dispensing system 303, in accordance with an embodiment of the invention. Like reference numerals have been used to designate functionally similar components. The third exemplary fluid dispensing system 401 includes three valve assemblies 201a-c similar to the valve assemblies 201a-h of the second exemplary fluid dispensing system 303. Other numbers of valve assemblies may be employed. In contrast to the second exemplary fluid dispensing system 303, the third exemplary fluid dispensing system 401 includes a DI-water input 402 (e.g., in the manifold 225), which is coupled to the input 221a-c of a second valve 205a-c included in each of the valve assemblies 201a-c via a check valve 403 adapted to permit one-way flow of fluid. As shown in FIG. 4, the DI water path 223 is coupled to and extends through the inputs 221a-c of the second valves 205a-c of each of the valve assemblies 201a-c.

Further, the outputs 213a-c of the valve assemblies 201a-c are each coupled to a pressure transducer 405a-c for measuring incoming pressure (e.g., the pressure of a chemical or DI water output from the third exemplary fluid dispensing system 401). Each output 213a-c of the valve assemblies 201a-c also is coupled to a slurry or chemical dispense module 407a-c.

The foregoing description discloses only exemplary embodiments of the invention. Modifications of the above disclosed apparatus and methods which fall within the scope of the invention will be readily apparent to those of ordinary skill in the art. For example, one or more of the pneumatically-actuated valves of the present fluid dispensing systems 101, 303, 401 may be remotely actuated, (e.g., by software). The fluid dispensing system 101, 303, 401 may be fabricated from chemically resistant materials such as PTFE (e.g., Teflon®), PFA, or other high purity polymers. Other valve materials also may be employed. In one embodiment, a plurality of second exemplary fluid dispensing systems 303 may be coupled together (e.g., connected in a row). A removable DI water supply fitting may be coupled to the DI water input 220 of the first fluid dispensing system 303 in the row. Similarly, a removable DI water return fitting may be coupled to the DI-water-return output 301 of the last fluid dispensing system 303 of the row.

In one or more embodiments, the first input 207 and the first output 209 of the first valve 203 are included on the same side of the manifold 225, thereby facilitating connections to the chemical supply 103 and chemical return 107. Further, the first valve 203 of each of the valve assemblies 201 of the fluid dispensing system 101, which includes the manual override switch 215, may be positioned at the bulkhead of the fluid dispensing system 101, thereby reducing the need for additional manual valves. The first valves 203 may be positioned differently.

Accordingly, while the present invention has been disclosed in connection with exemplary embodiments thereof, it should be understood that other embodiments may fall within the spirit and scope of the invention, as defined by the following claims.

The invention claimed is:

1. An apparatus adapted to provide fluid to a semiconductor device processing apparatus tool, comprising:
a single-piece fluid dispensing system including:
a plurality of valve assemblies, each of the plurality of valve assemblies including:
a valve assembly output adapted to output at least one of DI water and a chemical;
a first valve comprising:
a first input adapted to receive the chemical;
a first output adapted to circulate the chemical to a chemical return; and
a second output adapted to output the chemical to the valve assembly output;
a second valve positioned downstream from the first valve comprising:
an input adapted to receive deionized (DI) water; and
an output adapted to output DI water to the valve assembly output; and
a check valve coupled between the second output of the first valve and the output of the second valve;
wherein the first valve, second valve and check valve are included in a single manifold; and
wherein each of the valve assembly outputs is adapted to connect to a separate dispense module.

2. The apparatus of claim 1, wherein each of the plurality of valve assemblies further comprises a DI water return output adapted to circulate the DI water to a DI water return.

3. The apparatus of claim 1, wherein the apparatus is included in the semiconductor device processing apparatus.

4. The apparatus of claim 1 wherein the first valve further comprises a manual override switch.

5. The apparatus of claim 1 wherein at least one of the first and second valves is a pneumatically-actuated valve.

6. The apparatus of claim 1 wherein one or more DI water path within each of the plurality of valve assemblies includes no dead leg.

7. The apparatus of claim 1 wherein the first input and the first output of the first valve are on a same side of the manifold.

8. The apparatus of claim 1 wherein a size of the first output of the first valve is smaller than a size of the first input of the first valve.

* * * * *